(12) United States Patent
Morris (10) Patent No.: US 8,701,506 B2
(45) Date of Patent: Apr. 22, 2014

(54) LIQUID SAMPLING APPARATUS

(76) Inventor: James O. Morris, Spanaway, WA (US)

(*) Notice: Subject to any disclaimer, the term of this patent is extended or adjusted under 35 U.S.C. 154(b) by 1130 days.

(21) Appl. No.: 11/347,471

(22) Filed: Feb. 3, 2006

(65) Prior Publication Data

US 2007/0180934 A1 Aug. 9, 2007

(51) Int. Cl.
*G01N 1/00* (2006.01)

(52) U.S. Cl.
USPC ..................................... 73/863.86

(58) Field of Classification Search
USPC .............. 73/863.81, 863.85, 864.63, 864.73, 73/864.74, 863.82, 863.57, 863.53, 73/863.54, 863.55, 863.84; 141/351
See application file for complete search history.

(56) References Cited

U.S. PATENT DOCUMENTS

| | | | | |
|---|---|---|---|---|
| 3,858,449 A * | 1/1975 | Singer | ........................ | 73/863.83 |
| 4,289,027 A * | 9/1981 | Gleaves et al. | ................. | 73/299 |
| 4,524,811 A * | 6/1985 | Taylor | .......................... | 141/325 |
| 4,580,453 A * | 4/1986 | Taylor | ........................ | 73/863.86 |
| 4,598,581 A * | 7/1986 | Brekke | ........................ | 73/117.3 |
| 4,846,269 A | 7/1989 | Schnatzmeyer | | |
| 5,200,149 A | 4/1993 | Fisher | | |
| 5,200,151 A | 4/1993 | Long | | |
| 5,261,285 A * | 11/1993 | Tokoyama | ................... | 73/865.8 |
| 5,313,824 A | 5/1994 | Herguth et al. | | |
| 5,506,501 A * | 4/1996 | Fogel et al. | ................... | 324/204 |
| 5,551,310 A * | 9/1996 | Formica et al. | ............ | 73/863.86 |
| 5,823,222 A * | 10/1998 | Minshull et al. | ............ | 137/15.15 |
| 6,101,201 A * | 8/2000 | Hargis et al. | ..................... | 372/36 |
| 6,899,315 B2 * | 5/2005 | Maiville et al. | ............. | 251/149.4 |
| 2005/0061484 A1 * | 3/2005 | Hendricks et al. | ........ | 165/104.21 |
| 2007/0150161 A1 * | 6/2007 | Dequenne | ..................... | 701/101 |

OTHER PUBLICATIONS

Allen, Aircraft Products, Inc. Sales Catalogue, Ravenna, Oh. (8 pages) (undated).
Orsagh, R; Sheldon,J. et al, Prognostics/Diagnostics for Gas Turbine Engine Bearings, Impact Technologies, LLC, Rochester, N.Y. (10 pages) (undated).
Department of the Army Technical Bulletin, Aeronautical Equipment, Army Oil Analysis Program (AOAP), Headquarters, Department of the Army, Washington, D.C., Apr. 10, 1987; TB 43-0106 (25 pages).

* cited by examiner

*Primary Examiner* — Robert R Raevis
(74) *Attorney, Agent, or Firm* — R. Reams Goodloe, Jr.

(57) ABSTRACT

A liquid sampling apparatus. The liquid sampling apparatus includes a body, a first port, and a second port, and a liquid conduit therebetween. A nose portion is provided adjacent the first port sized and shaped for interfitting engagement with, and for opening of, a biased normally closed outlet valve in a liquid reservoir. When liquid is allowed to exit a liquid reservoir, the sampling apparatus allows flow of the liquid between the ports. The body may be provided having a flexible portion, allowing the second port to be directed at a sampling container. The liquid sampling apparatus maybe constructed in polyethylene or other material suitable for use with the liquid being sampled, such as lubricant.

54 Claims, 6 Drawing Sheets

FIG. 12

LIQUID SAMPLING APPARATUS

TECHNICAL FIELD

This invention relates to the field of liquid sampling.

BACKGROUND

In lubricants for mechanical systems, both the first appearance and the ongoing presence of metal particulates can be an indication of impending failure. Lubricant composition may be especially revealing in lubrication fluids in some mechanical systems such as gear boxes, transmissions, hydraulic systems, or engines. When such systems are in aircraft, flight safety requirements dictate that regular and thorough oil analysis be conducted. To assist in detecting the presence of metals in such systems, and in particular, the presence of metal particulates, detectors have been developed. Such detectors are commonly called chip detectors, since they detect metal chips. Many chip detectors are designed to allow flow of lubricant through, or around, a portion of the detector. Chip detectors include sensors for detecting the presence of chips, and provide an indication upon first appearance of, and during ongoing presence of, metal particulates. Chip detectors provide a significant benefit in assisting maintenance and operations personnel in averting potential catastrophic failure. However, there remains a need to obtain lubricant samples to observe metal wear rates in mechanical parts via the metal content of spent lubricants (whether in particulate form, or in dissolved form, or in a complexed form, or in other form), or to verify the absence of metal particulates, or in the case when activation of a chip detector alarm has occurred, to verify the presence of metal particulates. In other words, in addition to observation of wear rates in mechanical equipment, an important reason for sampling is to verify the correct operation of chip detectors. Thus, many aircraft lubricant systems include self-closing valves that facilitate frequent lubricant sampling. Resulting lubricant samples are sent to oil analysis laboratories. Based on the report of a particular lubricant sample, further action may be taken, as appropriate.

Unfortunately, taking samples from many self-closing valves continues to be a messy and time consuming job. Often, makeshift equipment is utilized. For example, in military field operations, plastic tubing intended for medical applications may be cut up in lengths suitable for extraction of oil samples. This is time consuming, and uses up expensive supplies intended for other uses. And, regardless of the sophistication of such improvised measures, quite often a messy and potentially dangerous oil release occurs, either on to aircraft parts, some of which may be hard to reach or to clean, or into the adjacent environment. Consequently, there remains a significant and as yet unmet need for a simple, reliable, low cost, and effective oil sampling device which is especially adapted for use with quick-release valves, as often found in aircraft chip detectors.

BRIEF DESCRIPTION OF DRAWING

The present invention will be described by way of exemplary embodiments, illustrated in the accompanying drawing in which like references denote similar elements, and in which.

The foregoing figures, being merely exemplary, contain various elements that may be present or omitted from actual embodiments which may be implemented, depending upon the circumstances. Further, similar parts may be denoted with similar symbols, but utilizing a "prime" symbol as a suffix—"'"—and these shall be considered the functional equivalent of similar parts without such prime suffix symbols thereafter, as such nomenclatures is utilized in order to avoid unnecessary duplicate explanation of components or of the function thereof, especially as utilized shown in FIG. 6, for example. An attempt has been made to draw the figures in a way that illustrates at least those elements that are significant for an understanding of the various embodiments and aspects of the invention. However, various other elements of a suitable liquid sampling apparatus may be utilized in order to provide a versatile liquid sampling apparatus for reliably extracting a lubricant sample from mechanical apparatus while minimizing or eliminating leakage of lubricant, in accordance with the teachings hereof and the claims set forth hereinbelow.

DETAILED DESCRIPTION

Figures 1, 2, 3:
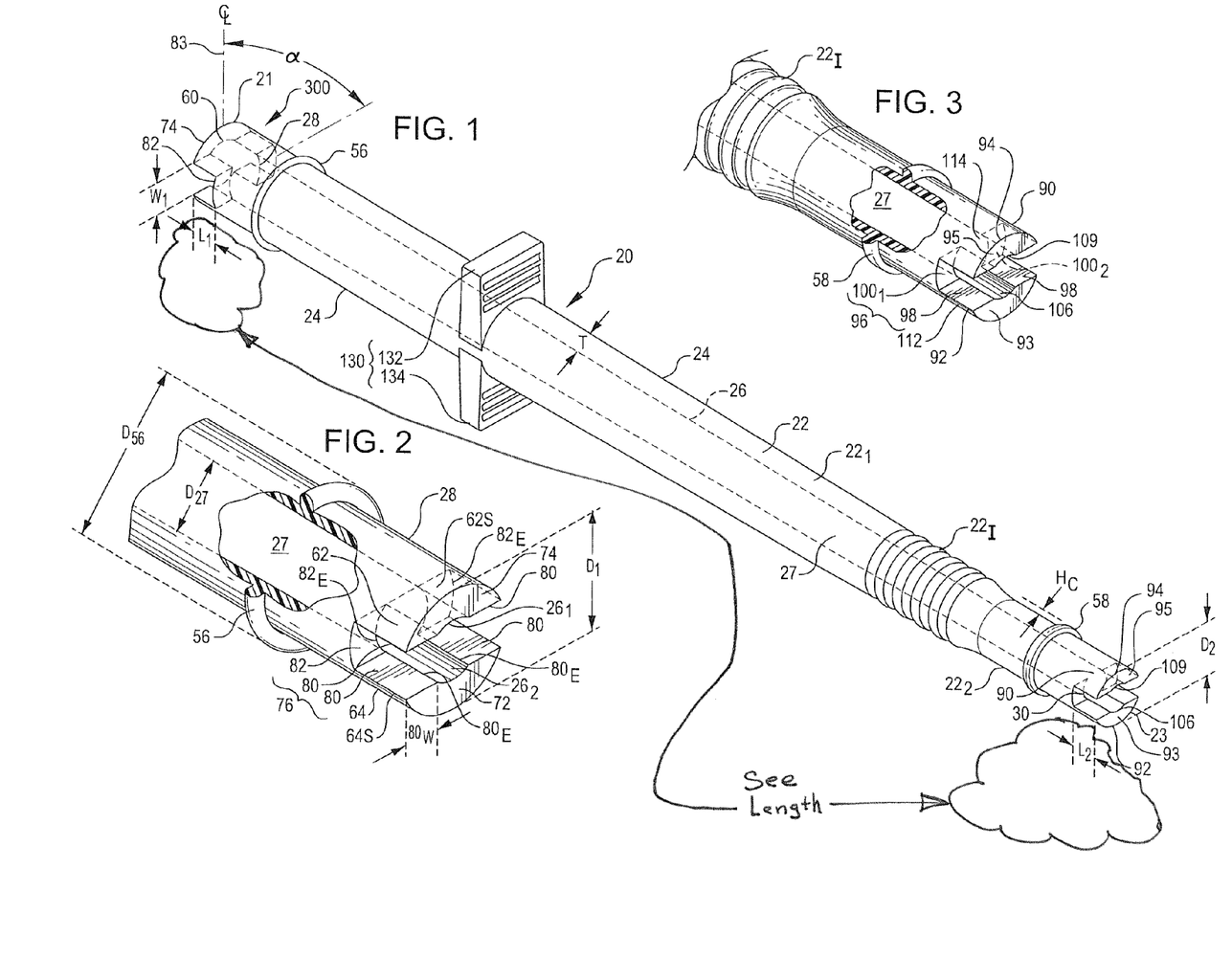
FIG. 1 illustrates a perspective view of a liquid sampling apparatus.
FIG. 2 illustrates an enlarged perspective view of a first end portion of a liquid sampling apparatus, showing a port for insertion into a sealable valve, in accordance with an embodiment of the invention.
FIG. 3 illustrates an enlarged perspective view of a second end portion of a liquid sampling apparatus, showing a second port for insertion in a sealable valve, in accordance with an embodiment of the invention.

Turning now to FIG. 1, a perspective view is provided of one embodiment for a liquid sampling apparatus 20. The liquid sampling apparatus 20 is provided for use in sampling of liquid 42, particularly lubricant fluid, from a liquid reservoir 44 (see FIG. 4) having a biased, normally closed and openable valve 40 or 40', generally of the type seen in FIGS. 5 and 7. The liquid sampling apparatus 20 has a body 22 extending between a first end 21 and a second end 23. The body has a first port 28 at or near the first end 21 and a second port 30 at or near the second end 23. The liquid sampling apparatus 20 has a body 22 with one or more body external sidewalls 24 and one or more body internal sidewalls 26. The body internal sidewalls 26 define a liquid conduit 27 between the first port 28 and the second port 30, providing fluid communication between first port 28 and second port 30. In one embodiment, the body 22 is made utilizing a flexible structural material, such as polyethylene.

The first end 21 includes at least one nose portion 62 sized and shaped for interfitting engagement with and opening of a valve 40. Adjacent the at least one nose portion 62, a nose passageway 76 is defined by one or more nose passageway wall portions 80 is provided and a proximal ledge 82. The nose passageway 76 is shaped and sized for receiving and routing liquid 42 to or from the first port 28.

Figures 4, 5:
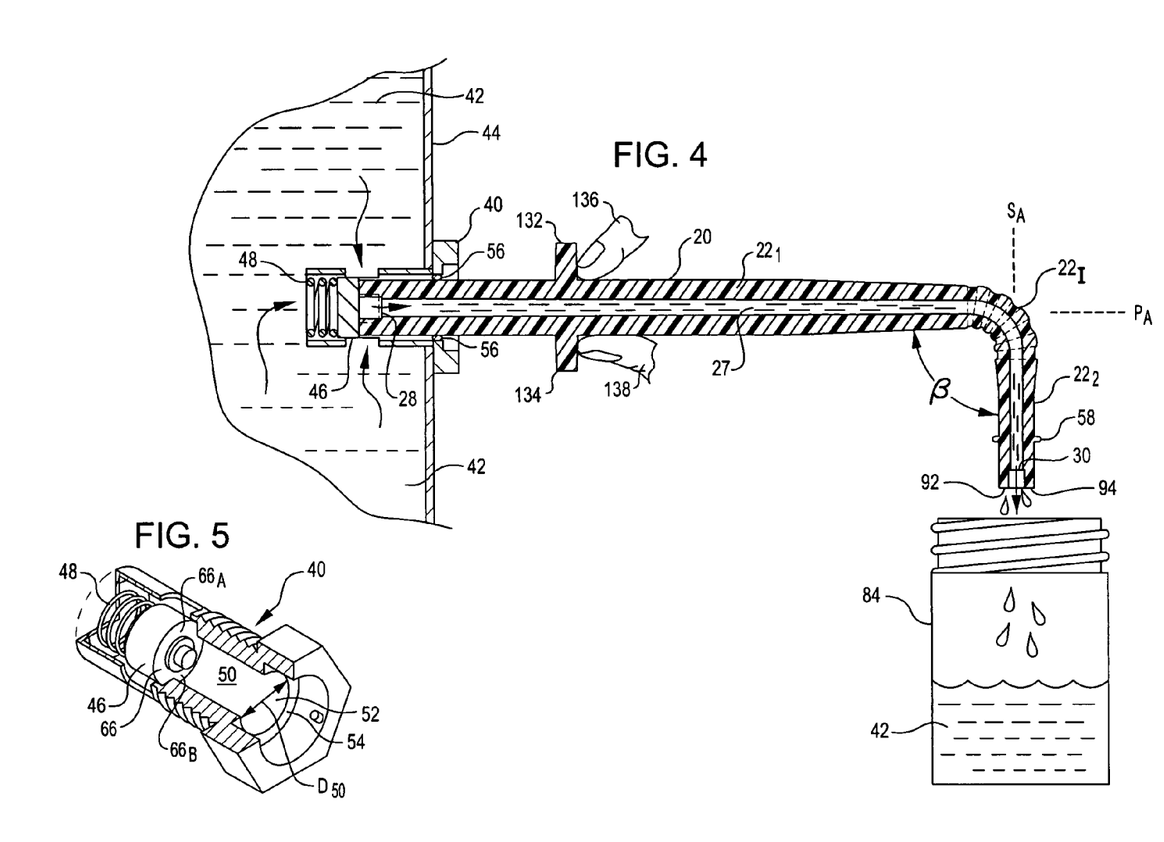
FIG. 4 provides a cross-sectional representation of an embodiment of a liquid sampling apparatus, wherein a first port of the liquid sampling apparatus has been engaged with a sealable valve in an oil reservoir, actuating the valve to open the valve and release oil from the reservoir, and wherein a portion of the oil being sampled is released and discharged into a sample container.
FIG. 5 illustrates a perspective view, with partial cut-away representation of one configuration for a sealable valve of the type just functionally illustrated in FIG. 4; this illustration is provided to enable to reader to understand one type of valve apparatus with which the liquid sampling apparatus disclosed and claimed herein may be advantageously utilized.
Figures 10, 11:
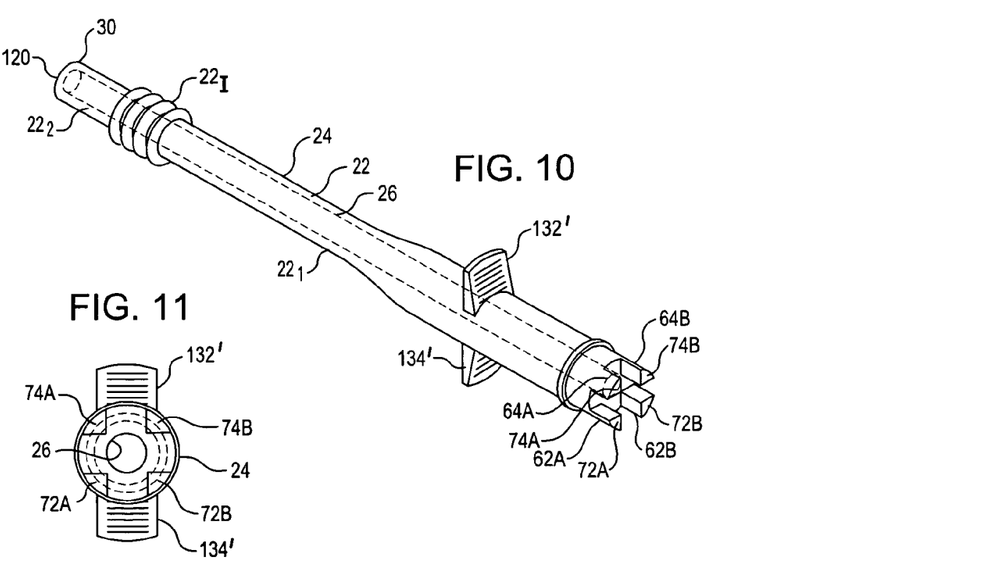
FIG. 10 illustrates yet another embodiment of a liquid sampling apparatus, similar to that just illustrated in FIGS. 8 and 9 above, but now showing the use of four nose portions, in accordance with an embodiment of the invention.
FIG. 11 illustrates an end view of the liquid sampling apparatus just set forth in FIG. 10, showing use of four nose portions, in accordance with an embodiment of the invention.
Figure 12:
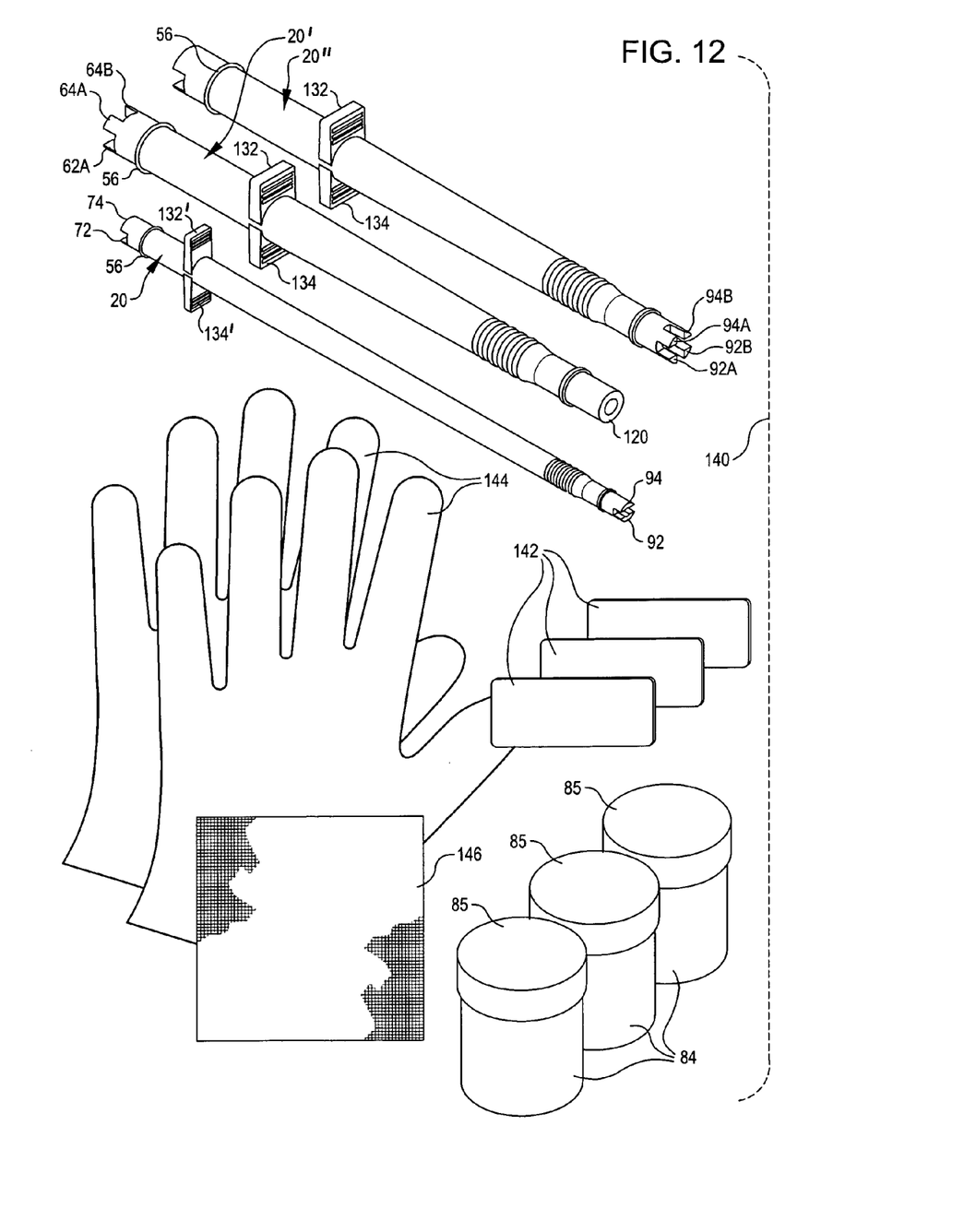
FIG. 12 represents the contents of a kit for practice an oil sampling method of using a liquid sampling apparatus as taught herein, showing various sizes and shapes for alternate embodiments of a liquid sampling apparatus as taught herein, as well as use of gloves (typically rubber), sample containers, labels, and a spill cloth for cleanup.

As is illustrated in more detail in FIG. 4, the first end 21 includes at least one nose portion or nose registration portion 62 that is sized and shaped for close mating engagement and yet insertable into a discharge passageway 50 of a first sealable valve 40. As variously noted in FIGS. 1 and 2, in some embodiments, two nose portions, 62 and 64 are provided, and which nose portions may be opposing first and second nose portion 62 and 64 elements. Further, as seen in FIGS. 10 and 12, four nose portions, identified as 62A, 62B, 64A, and 64B may be provided.

As shown in FIG. 5 the first sealable valve 40 may be an outlet valve for a first liquid 42 in a reservoir defined by reservoir walls 44. Typically, the liquid 42 being sampled is a lubricant oil.

In some embodiments, the body 22 of liquid sampling apparatus 20 has an external sidewall 24, that for at least a portion of length between the first port 28 and the second port 20, the internal sidewall 26 and the external sidewall 24 define therebetween a circular tubular body having a generally annular cross-sectional shape. Where a circular conduit configuration is utilized, the external sidewall 24 may be provided with an outer diameter $D_1$, as indicated in FIG. 2. Also, the internal sidewall 26 may in some embodiments be provided in a circular tubular configuration to define a tubular liquid conduit 27 having an internal diameter $D_{27}$, which diameter may vary in tapered tubular configurations. It should be understood that the body is not necessarily cylindrical, other than as may be necessary to fit the valve 40 or 40' being actuated. In some embodiments, for at least a portion of length between the first port 28 and the second port 30, the internal sidewall 26 and the external sidewall 24 define therebetween a sidewall thickness T for the body. In some cases, the sidewall thickness T decreases along at least a portion of such length.

Turning now to FIG. 5, a typical first sealable valve 40 with which the liquid sampling apparatus 20 is used includes a first sealable valve biased actuator 46. The first sealable valve biased actuator 46 may be biased by spring 48 to a normally closed position, as is illustrated in FIG. 5, to prevent the flow of liquid 42 from a reservoir defined by reservoir walls 44 as shown in FIG. 4 As discussed above, the first port 28 of the liquid sampling apparatus 20 may be inserted into the discharge passageway 50 of the first sealable valve 40. That discharge passageway 50 may be defined by a receiving sidewall 52 and an end wall 54. When passageway 50 is provided in a circular configuration, it may have a diameter $D_{50}$, as shown in FIG. 5. Similar configurations as shown in FIG. 7 for valve 40'.

In one embodiment of the liquid sampling apparatus 20, as shown in FIG. 4, a fluid sealing collar 56 protruding outwardly from external sidewall 24 of body 22 is shaped and sized for interfitting engagement with the receiving sidewall 52 of the first sealable valve 40. As FIG. 1 illustrates, fluid sealing collar 56 extends outwardly, and in one embodiment transversely in a U-shaped configuration, with the open end of the U affixed to, or integrally formed or molded with liquid sampling apparatus 20, from the body external sidewall 24. The nose fluid sealing collar 56 extends outward from the external sidewall 24 of the body 22 a distance sufficient so that the nose fluid sealing collar 56 is sealingly engageable with the valve 40. When provided in a circular configuration, the nose fluid sealing collar may have an outer diameter $D_{56}$, as seen in FIG. 2.

Figures 6, 7:
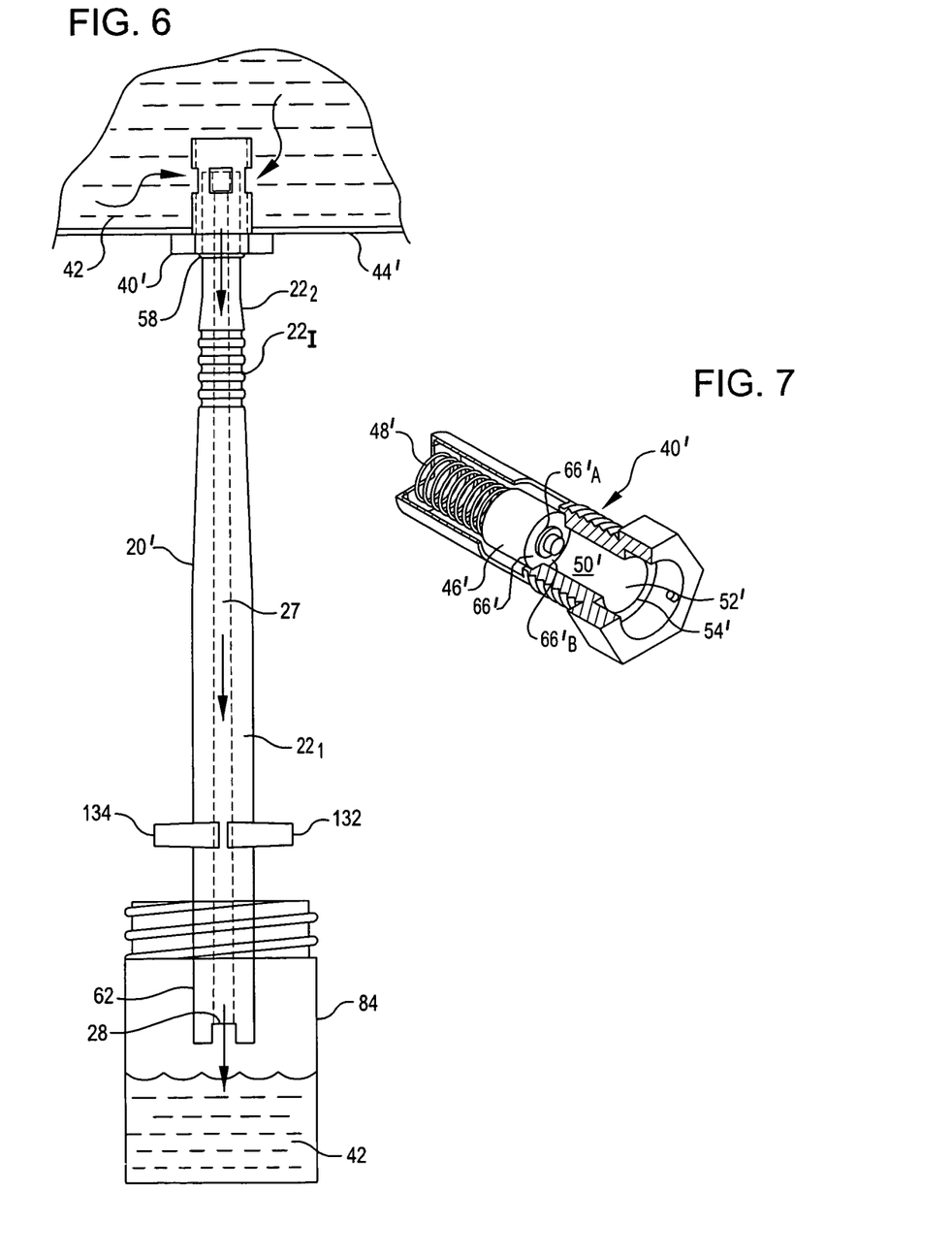
FIG. 6 provides a side elevation view of an embodiment of a liquid sampling apparatus, wherein a second port of the liquid sampling apparatus has been inserted into a sealable valve in an oil reservoir, actuating the valve to open the valve and release oil from the reservoir, and wherein a portion of the oil being sampled is released through a first port and discharged into a sample container.
FIG. 7 illustrates a perspective view, with partial cut-away representation of another configuration for a sealable valve of the type just functionally illustrated in FIG. 6; this illustration is provided to enable the reader to understand a type of valve apparatus with which the liquid sampling apparatus disclosed and claimed herein may be advantageously utilized.
Figures 8, 9:
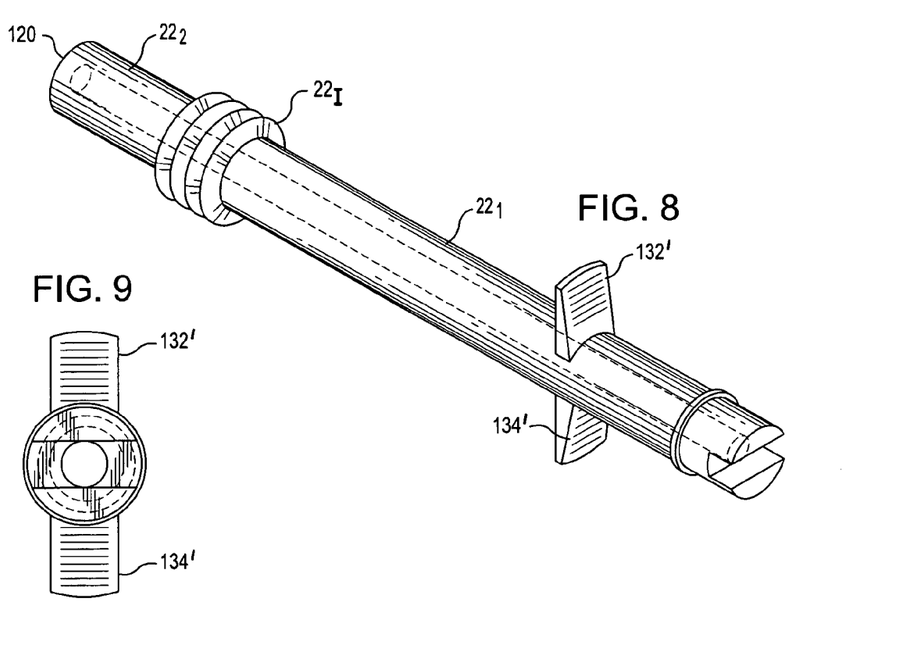
FIG. 8 provides a perspective view of another embodiment for a liquid sampling apparatus as disclosed and claimed herein, now showing use of a sampling port on only one end of the sampling device.
FIG. 9 illustrates an end view of the liquid sampling apparatus just set forth in FIG. 8, showing the use of two nose portions, in accordance with an embodiment of the invention.

In another embodiment, as shown in FIG. 6, a tail fluid sealing collar 58 extends outward from body external sidewall 24 a distance $H_C$ sufficient so that the fluid sealing collar 58 is sealingly engageable with the endwall 54' of the second sealable valve 40'. In this embodiment, tail fluid sealing collar 58 may be provided in the shape of an annular disc. The tail fluid sealing collar 58 extends outward from the external sidewall 24 of the body 22 a distance sufficient so that the tail fluid sealing collar 58 is sealingly engageable with the valve 40'. As shown in FIG. 6, the liquid conduit 27, within internal sidewalls 26, is sized and shaped to allow passage of the liquid 42 through the liquid sampling apparatus 20 after liquid 42 enters liquid sampling apparatus 20 through the second port 30.

FIGS. 1 and 2 illustrates a perspective view of one embodiment for the first port 28 of the liquid sampling apparatus 20. The first port 28 has a nose portion 60. As illustrated in the embodiment shown in FIG. 2, the nose portion 60 includes a first nose portion element 62 and a second nose portion element 64, each of which are sized and shaped, and include a transverse actuator engaging surface 74 on first nose portion 62, and a transverse actuator engaging surface 72 on second nose portion 64 for interfitting engagement with front end 66 of the biased actuator 46 of the first sealable valve 40 as illustrated in FIG. 5. As shown in FIG. 2, for one embodiment, the actuator engaging surfaces 72 and 74 have a substantially planar surface portion oriented transversely to the primary longitudinal axis $P_A$ (see FIG. 4) of the liquid sampling apparatus 20. In one embodiment, one or more of the at least one nose portions 62 and 64 have a length $L_1$ of a generally circumferential segment of a circular tube, and end at the transversely oriented planar actuator engaging surfaces 72 and 74. The transverse actuator engaging surfaces 72 and 74 (see FIG. 2) uniformly engage first $66_A$ and second $66_B$ (see FIG. 5) receiving portions of the front end 66 of biased actuator 46, to open the valve 40, so as to allow liquid 42 to escape through first sealable valve 40 and flow through first nose liquid entryway 76, and thence through first port 28 and into liquid conduit 27.

As illustrated in embodiments shown in the various figures provided, the actuator engaging surfaces 72 and 74 provide first opposing distal ledges 72 and 74. One or more nose liquid entry ways 76 are each defined by longitudinally extending nose entryway wall portions 80 and a first proximal ledge 82. As shown in FIG. 1, in one embodiment, the first proximal ledge 82 can be centered in a manner that it is offset at an angle alpha (α) of approximately ninety degrees from the centerline 83 of the actuator engaging surfaces 72 and 74. As illustrated in FIG. 2, a pair of first nose liquid entry ways 76 are provided, which are in this embodiment configured in an outwardly extending U-shaped wherein each prong of the U is provided by the longitudinally extending nose entryway wall portions 80 and the base of the U is provided by the first proximal ledge 82. As noted in FIG. 1, to further define the shape of each liquid entry way 76, the first proximal ledge may have a width $W_1$, and each prong of the longitudinally extending nose entryway portions 80 have a width 80W (see FIG. 2) and extend outwardly for a length $L_1$ (see FIG. 1) from first proximal ledge 82 to opposing distal ledges 72 and 74.

As shown in FIG. 2, the nose passageway 76 has an innermost or lower end wall 82 that may be provided in the shape of a proximal ledge. The first and second nose portion elements 62 and 64 extend outwardly a length $L_1$ from a lower end wall 82 of the nose passageway 76. The innermost edge 82E of lower end wall 82 adjoins the interior sidewall 26. In one embodiment, the innermost edge 80E of nose entryway portions 80 adjoins the interior sidewall 26. Thus, nose liquid entryway 76 is shaped and sized for receiving and routing the flow of liquid 42 from the first sealable valve 40 through nose liquid entryway 76, and thence into liquid conduit 27 in liquid sampling apparatus 20, for passage through liquid conduit 27 and discharge to a suitable sample container 84, as shown in FIG. 4. Containers 84 and caps 85 are also depicted in FIG. 12.

As illustrated in FIGS. 1, 2, and 3, the internal 24 and external 26 sidewalls of the liquid sampling apparatus 20 define the body 22 shape. As illustrated, one suitable embodiment for the body 22 shape is in the configuration of a tubular shape, which may be provided in a circular configuration with a generally annular cross-sectional shape. For some embodiments, the body 22 may be tapered along a primary longitudinal axis $P_A$. In such case, the internal sidewall 26 may define, in transverse cross-section at increasing distance from the first port 28, a liquid conduit 27 having decreasing cross-sectional area. Alternately, the thickness between external 26 and internal 24 sidewalls may vary while the cross-sectional area of liquid conduit 27 remains constant. However, various geometric shapes may be used and in the broadest context, the liquid sampling device is not limited to circular tubular shapes.

Returning to FIGS. 1 and 2 attention is again directed to the nose portion 28, which may have opposing first and second nose portion elements, 62 and 64 respectively. The first nose portion element 62 and second nose portion element 64 have first and second nose interior wall surface portions 26$_1$ and 26$_2$, that, in one embodiment are extensions of the internal sidewall 26 of the body 22. Further, in some embodiments, the first and second nose interior wall surfaces, 26$_1$ and 26$_2$ extend along at least a portion of surfaces of revolution that are co-extensive with the body internal sidewall 26. Additionally, first and second nose portion elements 62 and 64 have first and second nose exterior wall surfaces, 64S and 62S. In one embodiment, the first and second nose exterior wall surfaces 62S and 64S are extensions of, and extend along at least a portion of surfaces of revolution that are co-extensive with, the body external sidewall 24 of the body 22. In some embodiments, the first and second nose portion elements, 62 and 64, extend outwardly a length $L_1$ from the nose proximal ledge 82.

As further shown in the embodiment illustrated in FIGS. 1 and 3, the second port 30 of the liquid lubricant sampling apparatus 20 may include a tail portion 90. The tail portion 90 may have, for an embodiment, opposing first and second tail portion elements, 92 and 94, respectively which end at transverse valve engaging portions 93 and 95, respectively. At the tail portion 90, at least one a liquid discharge passageway 96 is defined by liquid discharge passageway wall portions 98 and by first tail proximal ledge 100$_1$. As exemplarily illustrated FIG. 3, the one or more liquid discharge passageway wall portions 98 for the liquid discharge passageway 96 can include a second tail proximal ledge 100$_2$ and a liquid discharge passageway wall portions 98.

The first tail portion element 92 and second tail portion element 94 have first and second tail interior wall surfaces, 106 and 109, respectively. In one embodiment, the first and second tail interior wall surfaces, 106 and 109 are extensions of the internal sidewall 26 of the body 22. Further, in some embodiments, the first and second tail interior wall surfaces, 106 and 109 extend along at least a portion of surfaces of revolution that are co-extensive with the body internal sidewall 26. Additionally, first and second tail portion elements 92 and 94 have first and second tail exterior wall surfaces, 112 and 114. In one embodiment, the first and second nose exterior wall surfaces 112 and 114 are extensions of, and extend along at least a portion of surfaces of revolution that are co-extensive with, the body external sidewall 24 of the body 22. In some embodiments, the first and second tail portion elements, 92 and 94, extend outwardly a length $L_2$ from the tail proximal ledges 100$_1$ and 100$_2$, respectively.

FIG. 3 illustrates that the versatility of the liquid sampling apparatus 20 may be enhanced by configuring the first and second tail portion exterior wall surfaces, 112 and 114 respectively, to have an outer diameter $D_2$ that is insertable into discharge outer passageway 50' of a second sealable valve 40' as illustrated in FIG. 7. The second sealable valve 40' has a second biased actuator 66' and a second discharge passageway 50' defined by a second receiving sidewall 52' and a second end wall 54'. The second biased actuator 66' is also normally closed to prevent the passage of liquid 42 yet openable to allow discharge of the liquid 42 therefrom. Liquid 42 noted in FIG. 6 may be the same as lubricant liquid 42 noted in FIG. 4, or a different liquid. First reservoir 44 shown in FIG. 4, and second reservoir 44' as shown in FIG. 6 may be any one of a variety of selected mechanical devices, such as in aircraft service, an engine oil reservoir, a main transmission oil reservoir, a tail gear box oil reservoir, a transfer case oil reservoir, and/or a hydraulic system oil reservoir. The first reservoir 44 or second reservoir 44' may be a part of a moveable vehicle (not shown). In some embodiments, the movable vehicle may be an aircraft. For example, the aircraft may be a helicopter, a tilt rotorcraft, an airplane, and an unmanned drone. In other embodiments, the moveable vehicle may be a water craft, and a ground vehicle.

As briefly noted above, the liquid sampling apparatus 20 has a body 22 having a first portion 22$_1$, an intermediate portion 22$_1$, and a second portion 22$_2$. The first portion 22$_1$ extends along a primary longitudinal $P_A$. The second portion 22$_2$ extends along a secondary longitudinal axis $S_A$. The body 22, in the area of the intermediate portion 22$_1$ is flexible, so that the first portion 22$_1$ and said second portion 22$_2$ are displaceable so that the primary longitudinal axis $P_A$ and the secondary longitudinal axis $S_A$ are offset. As seen in FIG. 4, sufficient flexibility between the primary longitudinal axis $P_A$ and the secondary longitudinal axis $S_A$ is provided, so that the first and second portions 22$_1$ and 22$_2$ of the body may be manually adjustable to an offset of an angle beta (β), and wherein said angle beta (β) is in the range from slightly less than 180 degrees (i.e., slight offset) to approximately 90 degrees (about a 90 degree offset).

In some embodiments, the body 20 is tapered along the primary longitudinal axis (see FIG. 10, for example). In such an embodiment, the internal sidewall 26 defines, in transverse cross-section at increasing distance from the first port 28, a liquid conduit 27 having decreasing cross-sectional area. In any event, in one embodiment, at or near the second port 30, the body has a cylindrical shape having an outer diameter $D_2$, and at or near the first end 28, the body has a cylindrical shape having an outer diameter $D_1$. In some embodiments, the outer diameter $D_1$ is larger than the outer diameter $D_2$.

As shown in FIG. 10, in some embodiments, at the second port 30, the body 22 has a cylindrical shape as just noted, but at the distal end, includes at least one transverse annular end surface portion 120. In other embodiments, as shown for example in FIGS. 1 and 3, the second port 30 has at least one tail portion 92, and in some embodiments, two tail portions 92 and 94, each of which are sized and shaped for interfitting engagement with and actuation of a biased, normally closed openable valve 40'. In other embodiments, the liquid sampling apparatus 20 has at least four tail portions. In one example, tail portions 72A and 72B, and 74A and 74B, are shown in FIG. 10. In another example, tail portions 92A and 92B, and 94A and 94B, are shown in FIG. 12.

Adjacent the at least one tail portion 92, a tail passageway 96 defined by one or more tail passageway wall portions 98 and end wall 100$_1$ or 100$_2$ is provided. The tail passageway 96 is sized and shaped for receiving and routing liquid 42 to or from the second port 30. In various embodiments, one or more of the at least one tail portions (e.g., 92 and 94) has a substantially planar tail surface valve engaging portions 93 and 95, respectively, for example, as set forth in FIG. 3. In many embodiments, the liquid sampling apparatus 20 is oriented along a longitudinal axis, and the substantially planar tail surface valve engaging portions 93 and 95 are oriented transverse to the longitudinal axis $S_A$. In some embodiments, each one of the at least one tail portions may have a length $L_2$ of a generally circumferential segment of a circular tube. As shown in FIGS. 1, and 3, the at least one tail portion comprises opposing first and second tail portions 92 and 94.

Generally, the liquid sampling apparatus 20 is manufactured from a low cost, easily disposable structural material. In any event, the structural material should be compatible with, and suitable for containment of the particular liquid hydrocarbon being collected. This hydrocarbon may be lubricating oil such as engine oil or transmission oil. The hydrocarbon for another embodiment may be a hydraulic fluid. For some embodiments, a suitable structural material such as polyethylene plastic can be used. For many embodiments, the liquid being collected is lubricating oil, especially aviation lubricating oils, and thus the structural material in such cases must be suitable for short term use therewith. One suitable material for such service is a polyethylene plastic. In various embodiments, the liquid sampling apparatus 20 may be manufactured of material selected from the group consisting of PTFE, polypropylene, polyethylene, and HDPE, or other materials having similar characteristics.

One advantage of such plastic materials is that they can be easily molded, and in such cases, the at least one nose portion 62 may be integrally molded in one piece with the body. Likewise, the at least one tail portion 92 may be integrally molded with the body. Further, the nose fluid sealing collar 56 and the tail fluid sealing collar 58 may be integrally molded with the body 22.

In various embodiments, it is useful to provide a finger brace 130, particularly one which extends outwardly from at least one side of the body 22. As illustrated in FIGS. 1 and 4, a finger brace 130 may have first 132 and second 134 finger brace portions. In one embodiment, the first 132 and second 134 finger brace portions extend transversely from opposing sides of said body 22. In one embodiment as illustrated in FIG. 4, the first 132 and second 134 finger brace portions are located spaced apart from, but in proximity to the first port 28. The first 132 and second 134 finger brace portions are gripable by a human user having a thumb 136 and index finger 138 (both shown in hidden lines in FIG. 4), so that when the user grips the body of said liquid sampling apparatus 20 between a thumb 136 and index finger 138, the thumb 136 and index finger 138 touch the first 132 and second 134 finger brace portions. In other figures, alternate finger brace configurations are indicated by reference numerals 132' and 134'.

In various embodiments, the first 62 and second 64 nose exterior wall surfaces 62S and 64S are disposed in opposing circular arc fashion, when the first end 28 has a diameter $D_1$ measured between the opposing first and second nose exterior wall surfaces 62S and 64S of one of the following: (a) approximately five-sixteenths inch, (b) approximately three-eighths inch, (c) approximately seven-sixteenths inch, (d) approximately one-half inch, (e) approximately nine-sixteenths inch, and (f) approximately three-fourths inch. However, these dimensions may differ to accommodate different interior dimensions for various sealable valves.

In various embodiments, the first and second tail portions 92 and 94 have exterior wall surfaces 112 and 114, respectively, which are disposed in opposing circular arc fashion. In one such embodiment, then the second end 30 has a diameter $D_2$ measured between opposing first and second tail portion exterior wall surfaces 112 and 114 of approximately five-sixteenths of an inch.

As earlier noted with respect to FIG. 4, a second port sealing portion is provided in the form of a tail fluid sealing collar 58 which extends outward from said external sidewall 24 of body 22 a distance sufficient so that the tail fluid sealing collar 58 is sealingly engageable with a receiving sidewall in valve 40'.

In FIG. 12, the components for a lubricant fluid sampling kit 140 for extracting lubricant fluid 42 from a mechanical system containing a lubricant fluid and having a lubricant discharge valve are illustrated. First, at least one, and in some embodiments, a plurality of containers 84 are provided, with caps 85. A label 142, and in some embodiments, a plurality of labels 142, sized and shaped for adhesive attachment to the container 84, are provided. A liquid sampling apparatus 20, or a plurality of the sampling devices 20, 20', and 20" may be provided, of various types as described herein. Further, at least one glove 144, and in some embodiments, a pair of gloves is provided. For cleanup, a liquid lubricant absorbent 146 may be provided.

Figure 13:
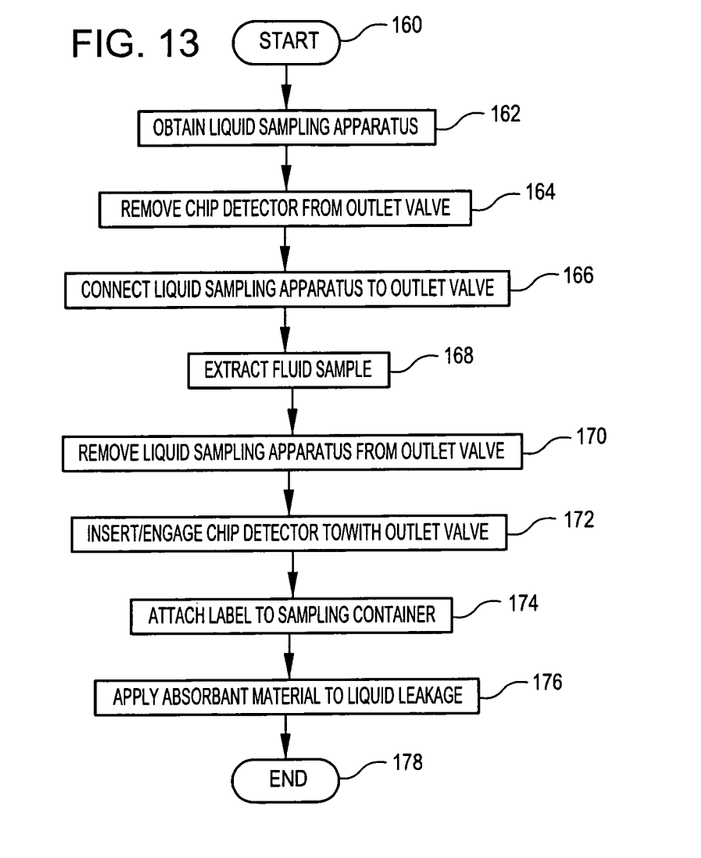
FIG. 13 provides a flow diagram of steps which may be useful in a method of taking liquid samples using the liquid sampling apparatus described herein.

FIG. 13 illustrates one process flow diagram for a sampling method utilizing a liquid sampling apparatus such as liquid sampling apparatus 20 illustrated in FIG. 1 above. At reference numeral 160, the process begins. A liquid sampling apparatus 20 is obtained, as indicated by reference numeral 162. Next, at reference 164, a chip detector fluidically coupled to a liquid reservoir 44 by an valve 40 may be removed. Next, at reference 166, the lubricant sampling apparatus 20 may be connected to the outlet valve fluidically couple to the liquid reservoir as illustrated in FIG. 4. Then, at 168, fluid aliquots are extracted from the liquid reservoir 44. In some embodiments, the coupling of the lubricant sampling apparatus to the outlet valve may cause the lubricant sampling apparatus 20 to manually actuate the outlet valve 40 and provide a non-contact depositing of the fluid sample, of a preselected volume, to a sample container 84. Next, as indicated at 170, the liquid sampling apparatus may be removed from the outlet valve. Next, at 172, the chip detector may be inserted and engaged with the outlet valve. Next, for some embodiments, at 174, a label may be attached to the sample container. Next, at for some embodiments, at 176, a lubricant absorbent, such as a cloth, or paper towel, may be applied to any liquid that may have leaked or discharged to remove the liquid from the reservoir 44, valve 40, and/or surrounding area. Next, at 178, for some embodiments, the process ends.

The method for the sampling operations described above with respect to the methods illustrated in FIG. 13 can be performed in a different order from those described herein. For example, it will be understood by those of ordinary skill that application of absorbent material 176 could be carried out prior to applying a label to a container at 174. Moreover, the operations described above with respect to the methods illustrated in FIG. 13 may be performed with omissions. For example, if no liquid is lost, then it will not be necessary to apply absorbent at 176 to clean up spilled liquid.

In any event, the just mentioned method may be used with a movable vehicle comprises a vehicle selected from the group consisting of an aircraft, a water craft, and a ground vehicle, and wherein said method further comprises connecting said lubricant sampling apparatus to the outlet valve to the lubricant reservoir in said selected vehicle. Further, the aircraft may be a helicopter, a tilt rotorcraft, an airplane, or an unmanned drone. Finally, the lubricant reservoir 44 may be an engine oil reservoir, a main transmission oil reservoir, a tail gear box oil reservoir, a transfer case oil reservoir, or a hydraulic system oil reservoir, or other oil containing reservoir that requires sampling.

In the foregoing description, for purposes of explanation, numerous details have been set forth in order to provide a thorough understanding of the disclosed exemplary embodiments for a liquid sampling apparatus, and for the distribution and use of a liquid sampling apparatus. However, certain of the described details may not be required in order to provide useful embodiments, or to practice a selected or other disclosed embodiments. Further, the description includes, for descriptive purposes, various relative terms such as adjacent, proximity, adjoining, near, on, onto, on top, underneath, underlying, downward, lateral, and the like. Such usage should not be construed as limiting. That is, terms that are relative only to a point of reference are not meant to be interpreted as limitations, but are instead included in the foregoing description to facilitate understanding of the various aspects of the disclosed embodiments of the present invention. And, various steps or operations in a method described herein may have been described as multiple discrete operations, in turn, in a manner that is most helpful in understanding the present invention. However, the order of description should not be construed as to imply that such operations are necessarily order dependent. In particular, certain operations may not need to be performed in the order of presentation. And, in different embodiments of the invention, one or more operations may be eliminated while other operations may be added. Also, the reader will note that the phrase "in one embodiment" has been used repeatedly. This phrase generally does not refer to the same embodiment; however, it may. Finally, the terms "comprising", "having" and "including" should be considered synonymous, unless the context dictates otherwise.

Importantly, the aspects and embodiments described and claimed herein may be modified from those shown without materially departing from the novel teachings and advantages provided by this invention, and may be embodied in other specific forms without departing from the spirit or essential characteristics thereof. Therefore, the embodiments presented herein are to be considered in all respects as illustrative and not restrictive or limiting. As such, this disclosure is intended to cover the structures described herein and not only structural equivalents thereof, but also equivalent structures. Numerous modifications and variations are possible in light of the above teachings. Therefore, the protection afforded to this invention should be limited only by the claims set forth herein, and the legal equivalents thereof.

The invention claimed is:

1. A liquid sampling apparatus, the liquid sampling apparatus for use with a liquid reservoir having a biased, normally closed and openable valve, said liquid sampling apparatus comprising:
   a body, the body extending between a first end and a second end, the body comprising a first port at or near the first end and a second port at or near the second end, the body comprising a flexible structural material and having an external sidewall and an internal sidewall, said internal sidewall defining a liquid conduit providing fluid communication between the first port and the second port;
   said first end further comprising at least one nose portion;
   adjacent said at least one nose portion, a nose passageway defined by one or more nose passageway wall portions, the nose passageway shaped and sized for receiving and routing liquid to or from the first port;
   adjacent said first port, a nose fluid sealing collar, said nose fluid sealing collar extending outward from said external sidewall distance sufficient so that said nose fluid sealing collar is sealingly engageable with said valve via application of manual pressure of said liquid sampling apparatus against said valve, and
   wherein one or more of said at least one nose portion is sized and shaped for interfitting engagement with and opening of the valve.

2. The liquid sampling apparatus as set forth in claim 1, wherein for at least a portion of length between said first port and said second port, the internal sidewall and the external sidewall define therebetween a circular tubular body having a generally annular cross-sectional shape.

3. The liquid sampling apparatus as set forth in claim 1, wherein for at least a portion of length between said first port and said second port, the internal sidewall and the external sidewall define therebetween a body having a sidewall thickness, said sidewall thickness decreasing along said at least a portion of length.

4. The liquid sampling apparatus as set forth in claim 1, wherein the first end comprises at least two nose portions.

5. The liquid sampling apparatus as set forth in claim 4, wherein the two nose portions comprise opposing first and second nose portion elements.

6. The liquid sampling apparatus as set forth in claim 1, wherein the first end comprises at least four nose portions.

7. The liquid sampling apparatus as set forth in claim 1, wherein one or more of said at least one nose portions comprises a substantially planar nose surface.

8. The liquid sampling apparatus as set forth in claim 7, wherein the body is oriented along a longitudinal axis, and wherein said substantially planar nose surface is oriented transverse to said longitudinal axis.

9. The liquid sampling apparatus as set forth in claim 1, wherein one or more of said at least one nose portion comprises a length $L_1$ of a generally circumferential segment of a circular tube.

10. The liquid sampling apparatus as set forth in claim 5, wherein said opposing first and second nose portion elements comprise first and second nose interior wall surfaces, and wherein said first and second nose interior wall surfaces are extensions of, and extend along at least a portion of surfaces of revolution that are co-extensive with, said internal sidewall of said body.

11. The liquid sampling apparatus as set forth in claim 5, wherein said nose passageway comprises a lower end, and wherein said first and second nose portion elements extend outwardly a length $L_1$ from a lower end of said nose passageway.

12. The liquid sampling apparatus as set forth in claim 1, wherein said nose fluid sealing collar is generally annular in cross-sectional shape.

13. The liquid sampling apparatus as set forth in claim 1, wherein said body comprises a first portion, an intermediate portion, and a second portion, and along said first portion extends along a primary longitudinal axis, and along said second portion extends along a secondary longitudinal axis, and wherein along said intermediate portion at least a portion of said body is flexible, so that said first portion and said second portion are displaceable so that said primary longitudinal axis and said secondary longitudinal axis are offset.

14. The liquid sampling apparatus as set forth in claim 13, wherein flexibility between said primary longitudinal axis and said secondary longitudinal axis is provided by a manually adjustable offset of an angle beta ($\beta$), and wherein said angle beta ($\beta$) is in the range from slightly less than 180 degrees to approximately 90 degrees.

15. The liquid sampling apparatus as set forth in claim 13, wherein said body is tapered along said primary longitudinal axis, and wherein said internal sidewall defines, in transverse cross-section at increasing distance from said first port, a liquid conduit having decreasing cross-sectional area.

16. The liquid sampling apparatus as set forth in claim 1, wherein at the second end, the body comprises a cylindrical shape having a transverse annular end surface portion.

17. The liquid sampling apparatus as set forth in claim 1, wherein the body, at or near the second end, comprises a cylindrical shape having an outer diameter $D_2$, and at or near the first end, the body comprises a cylindrical shape having an outer diameter $D_1$.

18. The liquid sampling apparatus as set forth in claim 17, wherein the outer diameter $D_1$ is larger than the outer diameter $D_2$.

19. The liquid sampling apparatus as set forth in claim 1, wherein
the second end further comprises at least one tail portion, the at least one tail portion sized and shaped for interfitting engagement with and actuation of a biased, normally closed openable valve; and
further comprising, adjacent said at least one tail portion, a tail passageway defined by one or more tail passageway wall portions, said the tail passageway shaped and sized for receiving and routing liquid from the second port.

20. The liquid sampling apparatus as set forth in claim 19, wherein the second end comprises at least two tail portions.

21. The liquid sampling apparatus as set forth in claim 19, wherein the second end comprises at least four tail portions.

22. The liquid sampling apparatus as set forth in claim 19, wherein one or more of said at least one tail portions comprises a substantially planar tail surface.

23. The liquid sampling apparatus as set forth in claim 22, wherein the body is oriented along a longitudinal axis, and wherein said substantially planar tail surface is oriented transverse to said longitudinal axis.

24. The liquid sampling apparatus as set forth in claim 19, wherein said at least one tail portion comprises a length $L_2$ of a generally circumferential segment of a circular tube.

25. The liquid sampling apparatus as set forth in claim 19, wherein said at least one tail portion comprises opposing first and second tail portions.

26. The liquid sampling apparatus as set forth in claim 1, wherein said body comprises a structural material suitable for containment of a liquid hydrocarbon.

27. The liquid sampling apparatus as set forth in claim 26, wherein said structural material comprises a material suitable for containment of lubricating oil.

28. The liquid sampling apparatus as set forth in claim 26, wherein said structural material comprises a polyethylene plastic.

29. The liquid sampling apparatus as set forth in claim 26, wherein said at least one nose portion is integrally molded in one piece with the body.

30. The liquid sampling apparatus of claim 1, wherein the liquid sampling apparatus is made of material selected from the group consisting of PTFE, polypropylene, polyethylene, and HDPE.

31. The liquid sampling apparatus as set forth in claim 1, further comprising a finger brace, said finger brace extending outwardly from at least one side of said body.

32. The liquid sampling apparatus as set forth in claim 31, wherein said finger brace comprises first and second finger brace portions, said first and second finger brace portions extending transversely from opposing sides of said body.

33. The liquid sampling apparatus as set forth in claim 32, wherein said first and second finger brace portions are located spaced apart from, but in proximity to said first port, wherein the first and second finger brace portions are gripable by a human user having a thumb and index finger, so that when the user grips the body of said liquid sampling apparatus between a thumb and index finger, the thumb and index finger touch the first and second finger brace portions.

34. The liquid sampling apparatus as set forth in claim 25, wherein said first and second tail portions comprise first and second tail exterior wall surfaces, and wherein said first and second tail exterior wall surfaces are extensions of, and extend along at least a portion of surfaces of revolution that are co-extensive with, said external sidewall of said body.

35. The liquid sampling apparatus as set forth in claim 10, wherein said first and second nose exterior wall surfaces are disposed in opposing circular arc fashion, and wherein the said first end has a diameter $D_1$ measured between said opposing first and second nose exterior wall surfaces, and wherein diameter $D_1$ is selected from the group consisting of (a) approximately five-sixteenths inch, (b) approximately three-eighths inch, (c) approximately seven-sixteenths inch, (d) approximately one-half inch, (e) approximately nine-sixteenths inch, and (f) approximately three-fourths inch.

36. The liquid sampling apparatus as set forth in claim 10, wherein said first and second nose exterior wall surfaces are disposed in opposing circular arc fashion, and wherein the first end has a diameter $D_1$ measured between said opposing first and second nose exterior wall surfaces of approximately one-half inch.

37. The liquid sampling apparatus as set forth in claim 34, wherein said first and second tail portion elements comprise first and second tail portion exterior wall surfaces, and wherein said first and second tail portion exterior wall surfaces are disposed in opposing circular arc fashion, and wherein first sealing port portion has a diameter $D_2$ measured between opposing first and second tail portion exterior wall surfaces is of approximately five-sixteenths of an inch.

38. The liquid sampling apparatus as set forth in claim 37, wherein said first and second tail portion exterior wall surfaces have an outer diameter $D_2$ size and shaped for insertion into an outer passageway of a sealable valve, and wherein the sealable valve has a biased actuator and a discharge passageway defined by a receiving sidewall and an end wall, and the biased actuator is normally closed to prevent the passage of liquid lubricant and openable to allow discharge of liquid lubricant therefrom;

said second port further comprising a tail sealing collar, second port sealing portion, said first and second tail portion elements of said second port sized and shaped for interfitting engagement with said second receiving sidewall and a tail portion having a tail actuator receiving surface for actuating engagement with said second biased actuator of the second sealable valve to actuate the second sealable valve to allow discharge of the liquid lubricant therefrom; and wherein said second port liquid discharge passageway said second port further comprising, adjacent said first and second tail portion, a second liquid lubricant entryway defined by one or more second entryway wall portions, said second liquid entryway shaped and sized for receiving and routing, to said liquid conduit, the liquid lubricants discharged from said second sealable valve when said second sealable valve is actuated to an open position.

39. The liquid sampling apparatus of claim 38, wherein the second port sealing portion comprises a tail fluid sealing collar said tail fluid sealing collar extending outward from said external sidewall of said body a distance sufficient so that said tail fluid sealing collar is sealingly engageable with said receiving sidewall.

40. A liquid sampling apparatus, for extraction of liquid from a liquid reservoir through an openable, engageable, biased normally closed and openable lubricant discharge valve, comprising:

a body, the body extending between a first end and a second end, the body comprising a first port at or near the first end and a second port at or near the second end, the body having an internal sidewall defining a liquid conduit providing fluid communication between the first port and the second port;

adjacent said at least one nose portion, a nose passageway defined by one or more nose passageway wall portions, the nose passageway shaped and sized for receiving and routing liquid to or from the first port;

wherein one or more of said at least one nose portion is sized and shaped for interfitting engagement with and opening of the valve;

wherein said body comprises a flexible structural material having a first portion, an intermediate portion, and a second portion, and along said first portion extends along a primary longitudinal axis, and along said second portion extends along a secondary longitudinal axis, and wherein along said intermediate portion at least a portion of said body is sufficiently flexible so that said first portion and said second portion are displaceable so that said primary longitudinal axis and said secondary longitudinal axis are offset; and a nose sealing collar for sealing the liquid sampling apparatus against the openable biased lubricant discharge valve so as to avoid leakage of lubricant fluid between the lubricant sampling apparatus and the openable biased lubricant discharge valve, when said at least one nose portion engages the openable biased lubricant discharge valve.

41. The liquid sampling apparatus of claim 40, wherein the lubricant sampling apparatus comprises a material selected from the group consisting of PTFE, polypropylene, polyethylene, and high density polyethylene.

42. The liquid sampling apparatus of claim 40, wherein said body comprises a tubular body.

43. The liquid sampling apparatus of claim 40, wherein said first port comprises a pair of first port nose actuator portions defined by opposing first distal ledges, and wherein said first port comprises a liquid entryway defined by first proximal ledges, and wherein said first proximal ledges and said opposing first distal ledges are offset approximately ninety degrees.

44. The liquid sampling apparatus of claim 40, wherein said second port further comprises a pair of second port tail actuator portions defined by opposing second distal ledges, and wherein said second port comprises a plurality of fluid discharge channels defined by second proximal ledges, and wherein said second proximal ledges and said opposing second distal ledges are offset by approximately ninety degrees.

45. A lubricant fluid sampling kit for extracting lubricant fluid from a mechanical system containing a lubricant fluid and having a lubricant discharge valve, said lubricant fluid sampling kit comprising:

a container, the container for holding lubricant fluid; and a liquid sampling apparatus, said liquid sampling apparatus comprising a body, the body extending between a first end and a second end, the body comprising a first port at or near the first end and a second port at or near the second end, the body comprising an internal sidewall defining a liquid conduit providing fluid communication between the first port and the second port, said first end further comprising at least one nose portion, and adjacent said at least one nose portion, a nose passageway defined by one or more nose passageway wall portions, the nose passageway shaped and sized for receiving and routing liquid to or from the first port, wherein one or more of said at least one nose portion is sized and shaped for interfitting engagement with and opening of the valve, and wherein said body comprises a flexible structural material having a first portion, an intermediate portion, and a second portion, and along said first portion extends along a primary longitudinal axis, and along said second portion extends along a secondary longitudinal axis, and wherein along said intermediate portion at least a portion of said body is sufficiently flexible so that said first portion and said second portion are displaceable so that said primary longitudinal axis and said secondary longitudinal axis are offset, and an external nose sealing collar for sealing the liquid sampling apparatus against the lubricant discharge valve so as to avoid leakage of lubricant fluid between the lubricant sampling apparatus and the lubricant discharge valve.

46. The liquid lubricant sampling kit of claim 45, further comprising at least one glove.

47. The liquid lubricant sampling kit of claim 45, further comprising a liquid lubricant absorbent.

48. The liquid lubricant sampling kit of claim 45, further comprising a label, said label sized and shaped for adhesive attachment to the container.

49. A method for delivering fluid lubricant from a lubricant reservoir to a sample container, comprising:
- obtaining a lubricant sampling apparatus having a fluid lubricant sealing collar;
- connecting said lubricant sampling apparatus to an outlet valve fluidically coupled to said lubricant reservoir, wherein the lubricant sampling apparatus provides a liquid conduit path extending from the outlet valve to a sample container;
- extracting fluid lubricant aliquots; and
- wherein connecting the lubricant sampling apparatus manually actuates the outlet valve and provides non-contact deposition of said fluid lubricant aliquots to said sample container during the fluid lubricant extraction, and
- wherein said outlet valve further comprises a chip detector fluidically coupled to the lubricant reservoir and wherein said method further comprises removing said chip detector from said outlet valve.

50. The method of claim 49, further comprising applying a lubricant absorbent to the leakage or discharge of the lubricant.

51. The method of claim 49, wherein said lubricant reservoir further comprises a moveable vehicle and wherein said method further comprises connecting said lubricant sampling apparatus to the outlet valve to the lubricant reservoir in said moveable vehicle.

52. The method of claim 51, wherein said movable vehicle comprises a vehicle selected from the group consisting of an aircraft, a water craft, and a ground vehicle, and wherein said method further comprises connecting said lubricant sampling apparatus to the outlet valve to the lubricant reservoir in said selected vehicle.

53. The method of claim 52, wherein said aircraft comprises a vehicle selected from the group consisting of a helicopter, a tilt rotorcraft, an airplane, and an unmanned drone, and wherein said method further comprises connecting said lubricant sampling apparatus to the outlet valve to the lubricant reservoir in said selected vehicle.

54. The method of claim 49, wherein the lubricant reservoir comprises a reservoir selected from the group consisting of an engine oil reservoir, a main transmission oil reservoir, a tail gear box oil reservoir, a transfer case oil reservoir, and a hydraulic system oil reservoir, and wherein said method further comprises connecting said sampling apparatus to the outlet valve to said selected reservoir.

* * * * *

UNITED STATES PATENT AND TRADEMARK OFFICE
CERTIFICATE OF CORRECTION

PATENT NO. : 8,701,506 B2  
APPLICATION NO. : 11/347471  
DATED : April 22, 2014  
INVENTOR(S) : James O. Morris Page 1 of 1

It is certified that error appears in the above-identified patent and that said Letters Patent is hereby corrected as shown below:

IN THE SPECIFICATION:

Column 2, line 28, after the word "enable", delete "to".

Column 2, line 45, after the words "a kit for", delete "practice" and substitute therefore --practicing--.

Column 6, line 15, after the word "illustrated", insert --in--.

Column 9, line 2, delete "couple" and substitute therefore --coupled--.

Signed and Sealed this  
Twenty-ninth Day of July, 2014

Michelle K. Lee  
*Deputy Director of the United States Patent and Trademark Office*